United States Patent [19]

Redding

[11] 4,179,929
[45] Dec. 25, 1979

[54] TRUCK SAMPLING SYSTEM

[76] Inventor: James A. Redding, 615 Washington Rd., Pittsburgh, Pa. 15228

[21] Appl. No.: 926,742

[22] Filed: Jul. 21, 1978

[51] Int. Cl.² ............................................. G01N 1/08
[52] U.S. Cl. ..................................... 73/423 R; 73/424
[58] Field of Search ............. 73/421 R, 421 B, 423 R, 73/424

[56] References Cited

U.S. PATENT DOCUMENTS

| | | | |
|---|---|---|---|
| 2,076,188 | 4/1937 | Thorsten | 73/424 |
| 3,751,991 | 8/1973 | Fisher | 73/424 |
| 3,841,161 | 10/1974 | Huntington | 73/421 R |

FOREIGN PATENT DOCUMENTS 521496 of 1977 U.S.S.R. ................................. 73/421 R

Primary Examiner—S. Clement Swisher
Attorney, Agent, or Firm—Clarence A. O'Brien; Harvey B. Jacobson

[57] ABSTRACT

Coal, and the like, contained in a truck is sampled by initially removing a core sample from the load, crushing the sample, dividing out an unwanted portion of the crushed sample, and returning the unwanted portion back to the load while the sample portion is delivered to a predetermined receptacle associated with a vender of the coal or other material forming the load. An auger mounted for reciprocation in a substantially vertical path and having a cutting head at the lower end is provided for cutting through the lumps of coal in order to obtain a representative sample.

12 Claims, 7 Drawing Figures

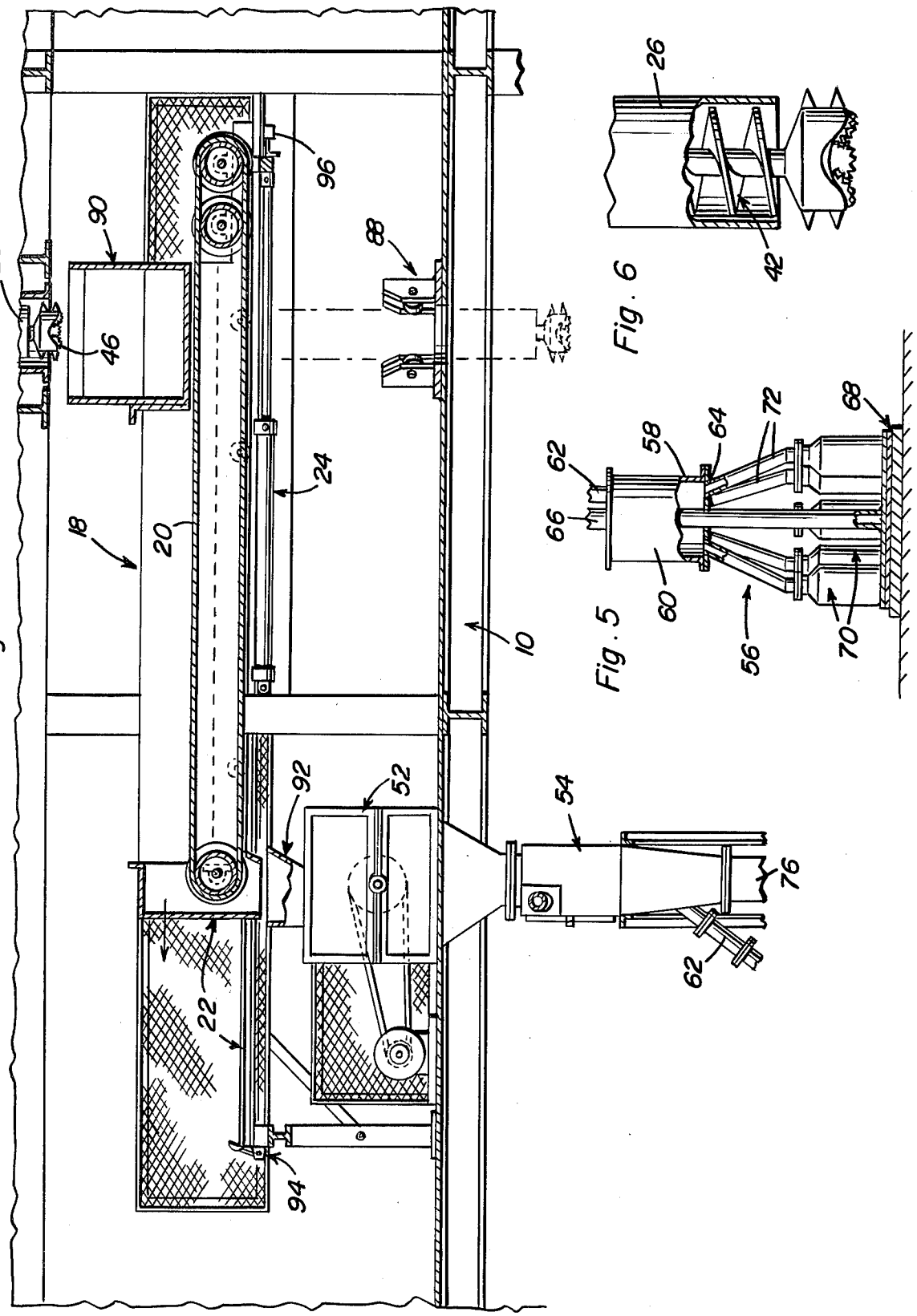

TRUCK SAMPLING SYSTEM

BACKGROUND OF THE INVENTION

1. Field of the Invention

This invention relates generally to the sampling of coal and similar materials, and particularly to the sampling of coal delivered by truck or other open conveyance for subsequent analysis to determine the quality of the coal.

2. Description of the Prior Art

Many coal consumers, particularly coal fired power generating plants, are receiving coal via trucks. The received coal is deposited into storage piles where it is not easily sampled for Btu's, sulfur, and other characteristics. The coal is usually received directly from a mine, and therefore the size of the coal and vary from large lumps to fines. There is no way known of adequately sampling truck received direct-from-mine coal.

More specifically, much of the coal which is received in such open trucks at power plants, and the like, is what is known as Run-of-Mine, generally abbreviated "ROM", coal. This coal is basically the product of a mine, which product has not been washed, prepared, screened, crushed, or sized. Coal received by a utility, for example, can be "ROM", or can be totally prepared, or can be sized, or any combination of these states depending upon economics and the burning characteristics of the coal. Nevertheless, since a substantial amount of the coal received is "ROM", there is a definite need for a sampler which has the capability of sampling such coal, and especially large size coal, and which is not limited to only a small sized coal sampling procedure.

The main and only goal in sampling is to obtain an unbiased sample from a given quantity of material that is accepted as a representative sample to both the seller and the buyer. This is best accomplished by extracting a true vertical core from the truck bed, rail car, or barge, when other methods of sampling are not applicable.

U.S. Pat. No. 3,158,030, issued Nov. 24, 1964 to G. B. Cross, discloses a mechanical coal sampler which employs a vertically disposed tube for reciprocal movement on a horizontally extending carriage in order to obtain a sample from a coal-laden truck and transferring the sample to a conveyor system for processing. This known sampler is typical of the prior art devices which only work satisfactorily on small sized lump product; in particular, lumps or pieces of material no larger than the size of the sampling tube. Further, U.S. Pat. No. 3,447,381, issued June 3, 1969 to R. W. Langtry et al, discloses a sampling mechanism which employs an auger, while U.S. Pat. No. 2,738,679, issued Mar. 20, 1967 to W. T. Senkowski, discloses a solid sampling apparatus which returns a discarded portion of a sample to the flow of product being sampled. The augers disclosed in U.S. Pat. No. 3,447,481, however, must dig through the coal bed, and in the process will take a path of least resistance which will not represent a true vertical core and will produce probable bias, since the only driving force downward is the weight of the device itself. U.S. Pat. No. 2,738,679, discloses a sampler only applicable to a moving stream of material, such as the discharge from the discharge pulley of a conveyor belt. It returns a portion of the primary sample not retained to a main stream of the material, but this prior device is not applicable to the sampling of material from a stationary quantity thereof disposed in an open container such as a truck bed, rail car, or barge.

U.S. Pat. No. 457,145, issued Aug. 4, 1891 to H. L. Bridgman, disclosed as an ore sampling machine that divides a mass into two or more portions and has the capability to further divide the divided portions into further divisions, But, this machine is not applicable for use with extracting a sample from an open container such as a truck. Further, U.S. Pat. No. 523,731 issued July 31, 1894 to G. D. Potter, discloses ore sampling machinary which extracts a sample from the discharge end of a chain-type conveyor via a pivotal chute, and like the machine disclosed in U.S. Pat. No. 457,145 is not applicable for use in extracting samples from open container carriers, and the like.

U.S. Pat. No. 1,105,702, issued Aug. 4, 1914 to T. J. Sturtevant, discloses a crushing mill which includes an arrangement for dividing a crushed sample of a product, and this device suffers from the deficiencies of those patents discussed above as regards application to extracting samples from open container carriers. In a like manner, the coal sampling machine shown in U.S. Pat. No. 1,186,646, issued June 13, 1916 to L. L. Beeken, is constructed only for use in extracting a sample from a moving stream of a product being analyzed.

U.S. Pat. No. 1,591,092, issued July 6, 1926 to A. G. McGregor discloses a sampling apparatus which permits the percentage of a sample to be varied from time to time, but like the references discussed above is applicable only to extracting a sample from a moving stream of material.

U.S. Pat. No. 3,841,161, issued Oct. 15, 1974 to F. R. Huntington discloses an overhead, extensible sampling device wherein an auger is reciprocally disposed within a tubular casing so as to permit the auger to be extended from the casing and into a load of bulk solid disposed in a hopper car, on a conveyor belt, and the like.

SUMMARY OF THE INVENTION

It is an object of the present invention to provide a sampling system suitable for use in obtaining samples from a stationary quantity of coal, and the like, disposed in an open container such as a truck bed, a railroad gondola or hopper car, a barge, and the like.

Another object of the present invention is to provide a sampling system capable of handling large lumps or pieces of coal, and the like.

Still another object of the present invention is to provide a sampling system which will extract a truer vertical core from a load being sampled than known core sampler devices.

Yet another object of the present invention is to provide a sampling system which deposits a selected sample into a receptacle identified with a vender of a particular load of material being sampled.

These and other objects are achieved according to the present invention by providing a sampling system having: a supporting frame; a core removal section including a sampling tube vertically, reciprocally mounted on the supporting frame for gathering samples from a stationary load of bulk material; and, a processing section mounted on the frame for receiving a sample from the core removal section and processing the sample for subsequent analysis.

The sample tube of the core removal section is advantageously mounted on the frame for reciprocating movement along a substantially vertical path of travel toward and away from a load of bulk material to be sampled. A conveyor assembly mounted on the frame for reciprocating movement in a substantially horizontal plane between a position extending from beneath the sample tube to the processing means, and a position to one side of the vertical path of travel of the sample tube, selectively receives a core sample from the sample tube for transferring the sample to the processing section, while sequentially moving out of the vertical path of the sample tube to permit same to move downwardly into the load of material being sampled.

The sample tube preferably comprises a longitudinally extending casing hollow at a lower end thereof and reciprocately mounted on the frame, with an auger being rotatably mounted within the casing extending substantially along the entire length thereof. A cutting head is affixed to the auger at the lower end thereof so as to extend through the opening provided in the casing in order to initially engage the coal or other material being sampled and cut through the coal along a substantially vertical downward path. The casing is reciprocally mounted on the frame by a support arrangement including a tower in which is disposed a linear fluid motor which actuates a lift sheave assembly connected to the motor, tower, and casing for moving the casing upwardly and downwardly as a function of movement of the motor.

The processing section preferably comprises a crusher arranged for receiving the samples extracted from loads of material by the core removal section and subsequently crushing the sample before feeding same into a secondary sampler conected to the crusher. This secondary sampler separates out a predetermined portion of the crushed sample and rejects, or returns, the unwanted portion of the sample back to the load from which the sample was taken. The predetermined portion of the crushed sample is fed into a collector which places the predetermined portion into a receptacle identified with a vender of the load of material being sampled.

These, together with other objects and advantages which will become subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 4 is a schematic, enlarged, fragmentary, vertical sectional view taken generally along the line 4—4 of FIG. 2.

FIG. 5 is a schematic, enlarged, fragmentary side elevational view, partly broken away in vertical section, showing a sample-receiving collector for use with a sampling system according to the present invention.

FIG. 6 is a schematic, enlarged, side elevational view, partly broken away and in vertical section, showing in detail the lower end of an auger device of a sample tube according to the present invention.

DESCRIPTION OF THE PREFERRED EMBODIMENTS

Figure 1:
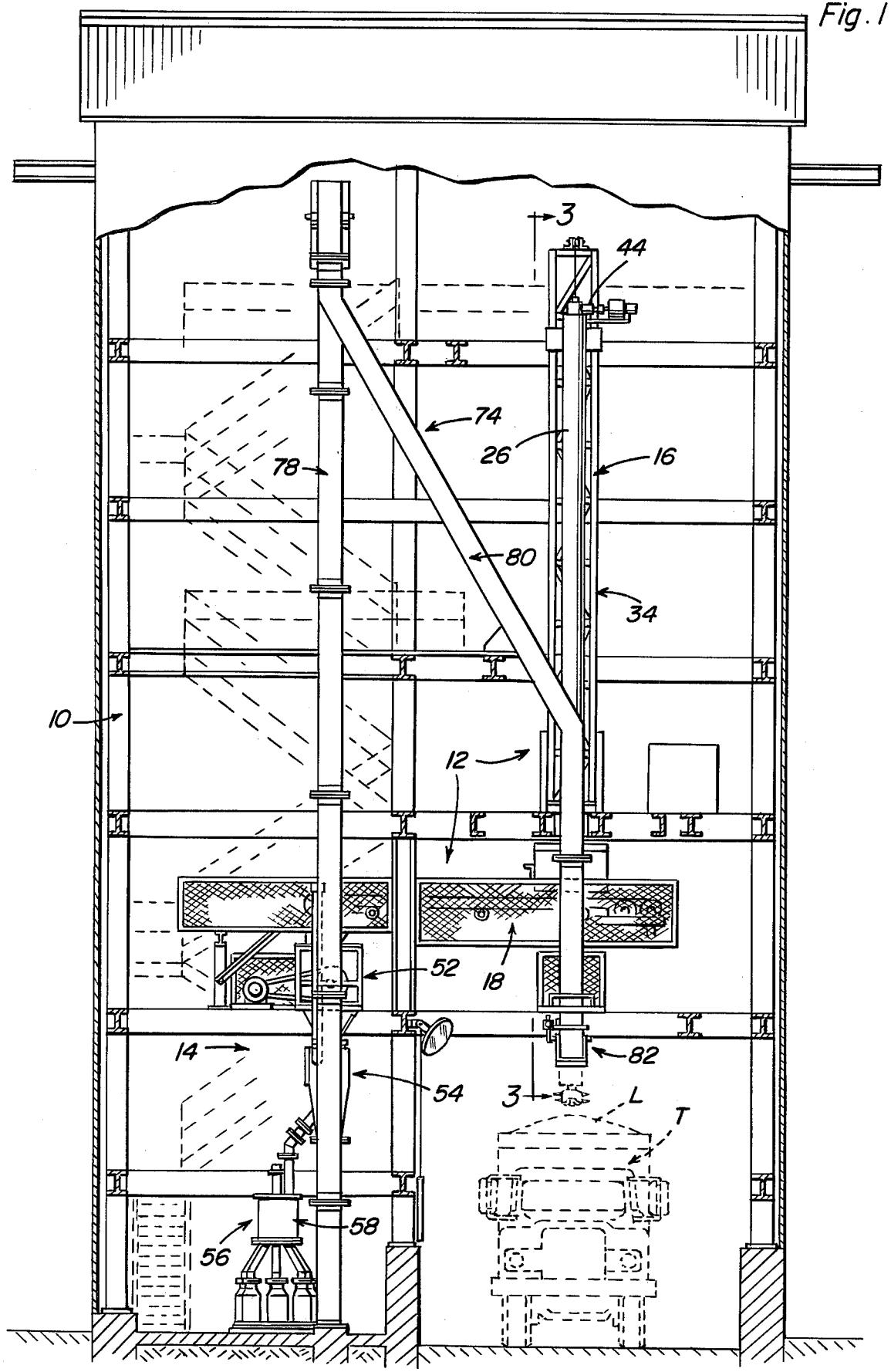
FIG. 1 is a schematic, front elevational view, partly cut away and in vertical section, showing a sampling system according to the present invention.
Figure 2:
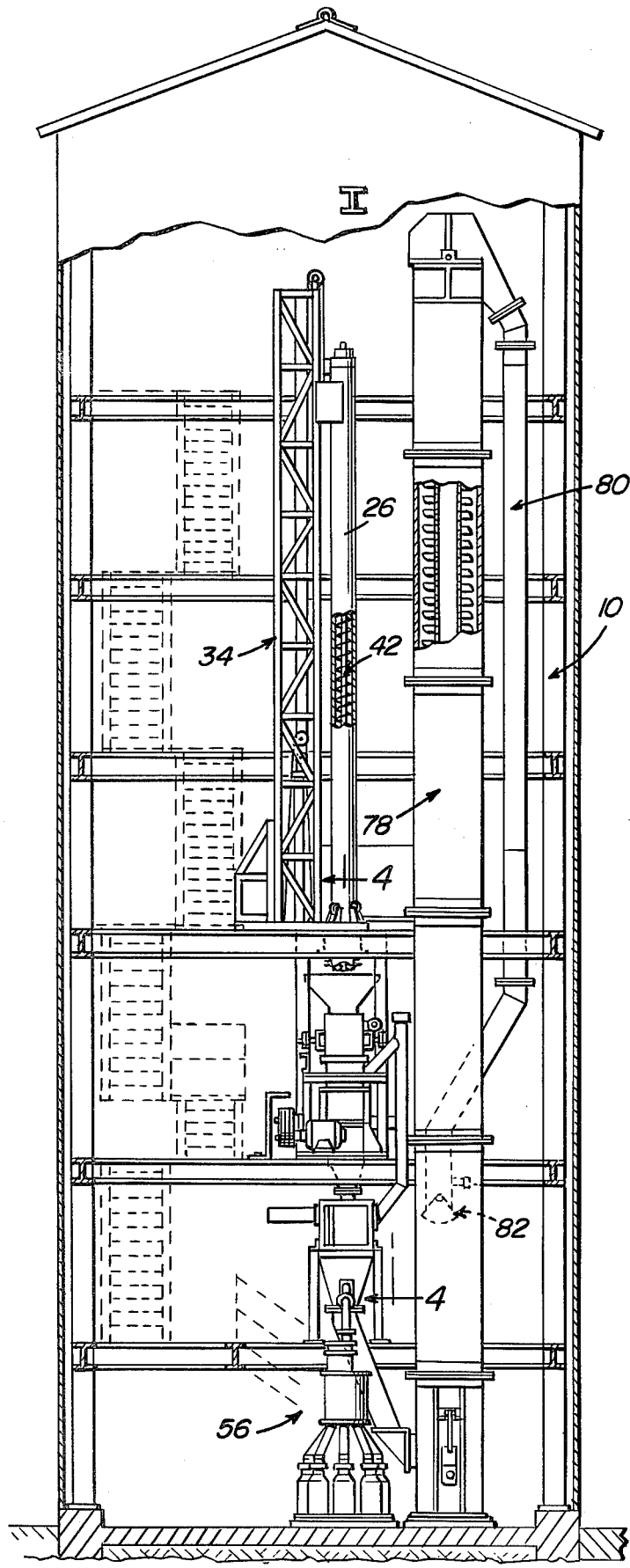
FIG. 2 is a schematic, side elevational view, partly cut away and in section, looking at a sampling system according to the present invention as seen from the left-hand side of FIG. 1.

Referring now more particularly to FIGS. 1-6 of the drawings, a sampling system according to the present invention is preferably built around and installed in a suitable structure including a framework such as that designated 10. This framework desirably has a roof disposed thereof and can have enclosing side walls as desired. The sampling system itself includes a core removal section 12 capable of removing a substantially true vertical core sample from a stationary load such as that designated L disposed in the open box of a truck T, and the like. Subsequent to core removal section 12 is a processing section 14 which will deliver a crushed portion of the sample taken in section 12 to a sample can identified with the vender of the load L being sampled.

The core removal section 12 includes a sample tube 16 mounted on framework 10 for reciprocating movement along a substantially vertical path of travel toward and away from load L of bulk material to be sampled. A conveyor assembly 18 including an endless belt 20 is also mounted on framework 10 for reciprocating movement in a substantially horizontal plane between a position extending from beneath sample tube 16 to processing section 14, and a position to one side of the vertical path of travel of sample tube 16 to permit the latter to move downwardly into load L being sampled. For this purpose, conveyor assembly 18 includes a carriage 22 in the form of a suitable frame rotatably mounting belt 20 and slidably disposed on rails affixed to framework 10. Reciprocation of carriage 22 is achieved by use of a conventional linear fluid motor 24 24, and the like.

Sample tube 16 includes a longitudinally extending casing 26 hollow at a lower end thereof and reciprocally mounted on framework 10 for movement toward and away from load L being sampled along the aforementioned substantially vertical path. More specifically, casing 26 is guided at all times by an auger guide assembly 28 disposed on a platform 30 mounted on a pair of horizontal beams of framework 10. A support assembly 32 is provided for reciprocally mounting casing 26 on framework 10, which assembly 32 includes a tower 34 vertically disposed on framework 10 and having disposed therewithin a conventional linear fluid motor 36, and the like, operatively connected to a lift sheave assembly 38 including a cable 40 and generally similar to a conventional block and tackle. One longitudinal end of the cable 40 is fastened to casing 26 at the upper portion thereof, as by the illustrated bracket, for controlling the vertical displacement of the casing 26.

A conventional auger 42 including an auger drive motor 44 is disposed in and mounted on casing 26 for vertical movement therewith, with a conventional cutting head 46 being connected to the lower end of auger 42 and disposed in the open lower end of casing 26 so as to protrude from the lower end of casing 26 and initially engage the material forming load L so as to cut through the material and insure a uniform flow of particles of reduced size into casing 26 in order to form the desired core sample between the inner walls of casing 26 and the auger 42. Suitable limit switches 48 and 50 are disposed on tower 34 adjacent the upper and lower portions thereof for controlling the travel of casing 26 in a known manner by a suitable electrical control system, and the like, not shown. Since the control system for sample tube 16 as well as conveyor assembly 18 and other parts of the sampling system, are of a conventional nature well known to practitioners of the art, and since these controls do not in themselves form part of the present invention, the control systems will not be described in greater detail herein. Further, the various stages of an operating cycle of the invention, as to be described below, can be actuated manually in the desired sequence.

The processing section 14 of a sampling system according to the invention includes a crusher 52 arranged for receiving a sample from the core removal section 12 and crushing this sample prior to feeding same to a secondary sampler 54. The latter separates from the crushed sample a predetermined portion thereof for feeding to a collector 56. The remainder or rejected portion of the sample is returned to load L in a manner to be described below.

Crusher 52 can be of a construction such as units commercially available, and an example of such a unit would be the "Jeffery" Model 30AB Hammermill with a 40 horsepower motor. Further, secondary sampler 54 can also be a commercially available unit, such as the "Wilmot" Model DTS-200-60 hydraulic secondary sampler.

Collector 54 includes an indexing arrangement 58 comprising a container 60 connected to secondary sampler 54 by a pipe 62 and having an outlet 64 arranged eccentrically to a centrally disposed, vertically arranged drive shaft 66 rotated in a suitable manner by a motor (not shown) and the like. Shaft 66 is journalled in a conventional manner on a planar base 68 which forms a turntable for a plurality of receptacles 70 forming the sample cans. Outlet 64 of container 60 is selectively indexed with a respective one of the receptacles 70 by the plurality of conduits 72 linking together the container 60 and receptacle 70.

Collector 56 also can be a commercially available unit, such as a "Galigher" eight position sample collector with a one-fourth horsepower drive and eight sample cans.

Figure 3:
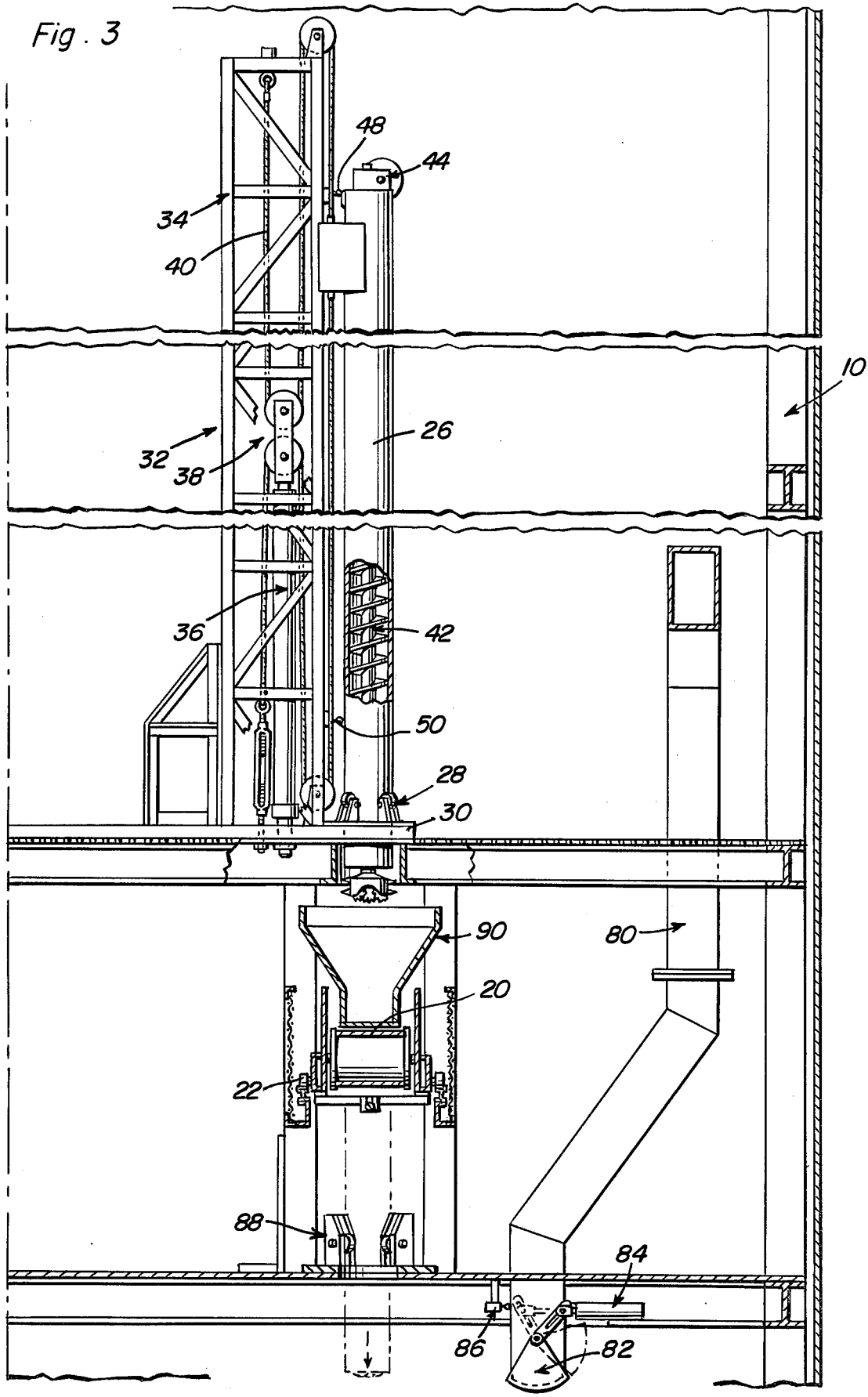
FIG. 3 is a schematic, enlarged, fragmentary, vertical sectional view taken generally along the line 3—3 of FIG. 1.

The processing section 14 further comprises material return arrangement 74 connected to the secondary sampler 54 as by the rejects chute 76 and including an elevator 78 of conventional construction and having a curved transition at the upper end thereof leading to a downwardly directed discharge chute 80. The latter terminates in a gate 82 selectively actuated by a fluid cylinder 84 of conventional construction. A conventional limit switch 86 is mounted on framework 10 for terminating the movement of the piston of fluid cylinder 84 when gate 82 has been moved to the broken line position as seen in FIG. 3. The purpose of gate 82 will be described below.

OPERATION

Figure 7:
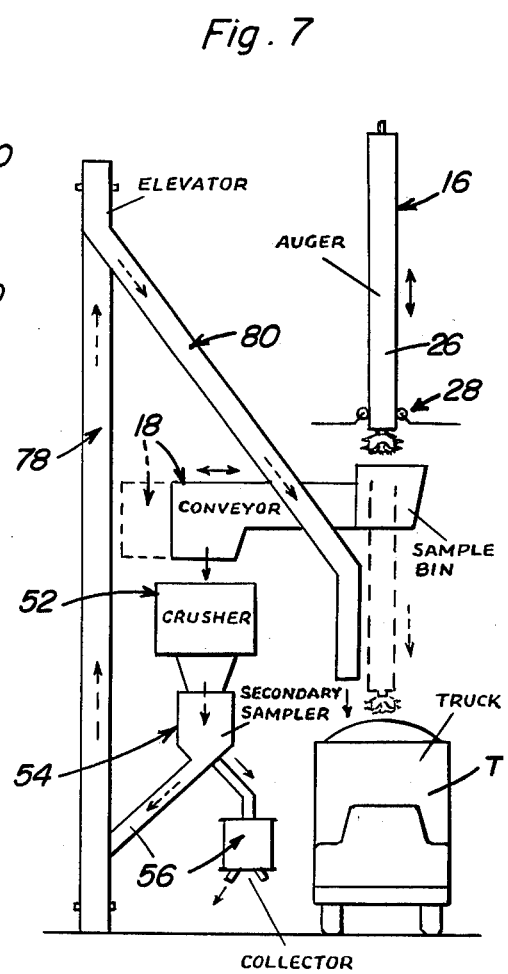
FIG. 7 is a schematic diagram showing a sampling system according to the present invention.

The operation of a sampling system according to the present invention will now be described with particular attention to FIG. 7 of the drawings. In the starting position, the sample tube 16 is in the upper portion as seen in full lines in FIG. 7. The conveyor assembly 18 is in the broken line position as seen in FIG. 7, while the discharge gate 82 of chute 80 is closed. Belt 20 of conveyor assembly 18 is moving to the left as seen in FIG. 4, while the sample crusher 52 and elevator 78 are operating and fluid under pressure is being supplied for actuating motors 24, 36 and 44.

An arriving truck T having been properly positioned, close to the right, close to the left, or centered as seen in FIGS. 1 and 7, the truck is stopped so that the auger 42 enters the coal forming load L close to the cab of the truck T, close to the gate thereof, or centrally of the load front to rear, with an infinite number of positions being possible. The stopping of truck T to the desired sampling position can be accomplished by signals, either given manually, by markers, or by signal lights. As soon as truck T is stopped, the operator (not shown) actuates the indexing arrangement 58 of collector 56 in a conventional manner (not shown) such as by manually turning the turntable formed by base 68, so that a receptacle 70 assigned to the vender of the coal truck sample about to be sampled is registered with the outlet 64 of container 60. The operator then actuates a starting button (not shown) which starts the auger drive motor 44 so as to commence rotation of auger 42 and the associated auger cutting head 46 in a predetermined direction which will cause the auger 42 and cutting head 46 to dig into load L as the sample tube 16 is dropped downwardly by appropriate movement of the motor 36 when sample tube 16 disengages from the limit switch 48, a red signal light (not shown), and the like, is actuated indicating that truck T must remain completely stopped. The sample tube 16 continues downwardly while guided along the desired vertical path by the guide assembly 28 until the lower end of casing 26 engages with the lower auger guide assembly 86. Now the sample tube 16 will be retained in a substantially rigid vertical orientation as the cutting head 46 engages load L being sampled. Auger cutting head 46, which may be similar in construction to a rock drill bit, cuts into the bed of coal in such a manner as to cut through lumps therein, with auger 42 conveying the cut coal upwardly into the auger casing 26. The sample tube 16 continues in a downward direction until casing 26 makes contact with limit switch 50 located so as to stop sample tube 16 with the lower end of casing 26 thereof as close to the bottom of the truck bed as practical. A vertical core of coal has now been extracted from the bed of truck T and is retained within casing 26. The latter is so dimensioned lengthwise so as to contain the desired volume of the extracted core of coal. This extracted core is the sample.

Upon contacting limit switch 50, auger 42, and therefore cutting head 46, cease to rotate by use of a, for example, conventional electrical switch (not shown) which closes off the flow of fluid under pressure to motor 44, and the entire sample tube 16 is then lifted upwardly veer a change in direction of motor 36 until the upper end of casing 26 makes contact with the limit switch 48. Closing of the latter mentioned limit switch 50 also causes the motor 24 to actuate and move carriage 22 toward the right to the full line position seen in FIG. 7. This movement locates inlet hopper 90 of conveyor assembly 18 directly beneath casing 26 of sample tube 16. The left-hand end of belt 20, as seen in FIGS. 4 and 7, will now be disposed immediately above a hopper 92 communicating with crusher 52. Movement of carriage 22 toward the right as seen in FIGS. 4 and 7 is stopped by contact with a limit switch 94, while leftward movement of carriage 22 is limited by switch 94, with both switches 92 and 94 being tied into the aforementioned conventional control system.

Conveyor assembly 18 upon making contact with switch 94 stops movement toward the right, and simultaneously closing of switch 94 actuates fluid cylinder 84 to move gate 82 into the chute 80 open position as illustrated in broken lines in FIG. 3. An adjustable timer (not shown) is now actuated, and simultaneously the red lights mentioned above are turned off and green lights (not shown) are turned on indicating that the truck T can move to a new position, still beneath the auger 42. Further, drive motor 44 is now actuated in reverse of its previous direction of rotation and the sample retained in casing 26 is conveyed downwardly by rotation of auger 42 onto belt 20 and conveyed thereby into hopper 92 of crusher 52. The adjustable timer is set to allow ample time for the entire sample to be exited from sample tube 16 and conveyed via belt 20 into crusher 52. When the timer times out, the timer activates the motor 24 so as to return carriage 22 toward the left as seen in FIGS. 4 and 7 until carriage 22 engages with limit switch 94. Upon making contact with limit switch 94, motor 24 is deactivated, thus stopping movement of carriage 22. Further, auger drive motor 44 now stops and is reset back into the forward rotation, in a conventional manner, ready to repeat the above sequence of operations.

Meanwhile, while the operations described immediately above are taking place, sample crusher 52 is crushing the sample to a fine size, like minus 8 mesh, and the crushed sample is discharged via the hopper at the bottom of crusher 52 into the secondary sampler 54. The latter extracts the desired quantity of final sample and diverts same into the piper 62 for transportation into the container 70 of indexing arrangement 58. Collector 56 has been previously properly indexed to receive the final sample into one of the receptacles 70 identified for the vender of the load being sampled. The amount of final samples can be adjusted in quantity of appropriate adjustment of the conventional secondary sampler 54.

The portion of the crushed sample which is not included in the final sample sent to collector 56 from the secondary sampler 54 is called rejects. The rejects are chuted via the chute 76 into elevator 78 and elevated vertically so as to be discharged into the discharge chute 80. Chute 80 is sized so as to have ample volume to hold more than the volume of rejects from a single sample truck T. The discharge chute gate 82 located at the end of chute 76 is opened by the activation of fluid cylinder 84, and upon opening makes contact with the aforementioned limit switch 86. Upon making contact with limit switch 86, a few seconds time delay relay (not shown) is activated, and when a time delay relay times out the fluid cylinder 84 is reversed so as to close gate 82. Thus, the quantity of rejects retained in discharge chute 76 is deposited into the truck T being sampled. Assuming the trucks have approximately equal depth of coal in the beds, the amount of loss in the weight of coal is minimal. The only loss in weight would be approximately the weight of the desired final sample extracted, which is generally a minimal amount.

SUMMARY

As can be readily understood from the above description and from the drawings, a sampling system according to the present invention permits a true vertical core to be taken from a stationary load, crushed, separated into an amount convenient for analysis, and deposited into a sample can identified with the vender of the load being sampled, with the rejects being returned to the load being sampled so as to minimize the loss in total weight of the load. Most importantly, "ROM" loads can be sampled since the sample tube of the invention is not limited by the size of the lumps or pieces of coal, and the like, constituting the load.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. A system for sampling a load of bulk material disposed on a stationary carrier, comprising, in combination:
   (A) a supporting frame;
   (B) core removal means vertically, reciprocally mounted on the frame for gathering samples from a bulk material disposed below the core removal means; and
   (C) processing means mounted on the frame for receiving samples from the core removal means and processing the samples for analysis of the quality of the material constituting the load;
   wherein the core removal means includes, in combination:
   (1) sample tube means mounted on the frame for reciprocating movement along a substantially vertical path of travel toward and away from a load of bulk material to be sampled; and
   (2) conveyor means mounted on the frame for reciprocating movement in a substantially horizontal plane between a position extending from beneath the sample tube to the processing means, and a position to one side of the vertical path of travel of the sample tube so as to permit the sample tube to travel downwardly toward the load being sampled.

2. A structure as defined in claim 1, wherein the sample tube means comprises, in combination:
   (a) a longitudinally extending casing hollow at a lower end thereof and reciprocatively mounted on the frame;
   (b) an auger rotatably mounted within the casing and extending substantially the entire length of the casing; and
   (c) a cutting head connected to the auger and disposed in the open end of the casing.

3. A structure as defined in claim 2, wherein the sample tube means further includes support means comprising a tower mounted on the framework, a linear fluid motor connected to the framework and disposed within the tower, and a sheave assembly connected to the motor and to the casing for moving the casing as a function of the movement of the motor.

4. A structure as defined in claim 3, wherein the processing means comprises, in combination:
   (3) crusher means for receiving a sample from the core removal means and crushing the sample;
   (4) secondary sample means connected to the crusher means for separating out a predetermined portion of the crushed sample; and
   (5) collector means for receiving the predetermined portion of the sample and retaining same for analysis.

5. A structure as defined in claim 4, wherein the collector means includes indexing means comprising a container connected to the secondary sampler means for receiving the predetermined portion of crushed sample, which container has an inlet and outlet; a plurality of receptacles disposed in circular arrangement beneath the container, the indexing means including a turntable on which the receptacles are disposed for being rotated in a substantially circular orbit; and conduit means including a plurality of chutes connected to the receptacles and extending toward the container for selectively registering with the outlet of the container.

6. A structure as defined in claim 5, wherein the processing means further comprises:
   (6) material return means connected to the secondary sampler means for returning to the load from which the sample was taken the sample less the predetermined portion of the sample retained for analysis.

7. A structure as defined in claim 6, wherein the material return means includes elevator means connected to the secondary sampler means for receiving the portion of the sample to be returned to the load from which it was taken, and elevating the portion of sample being returned, and a discharge chute arranged connected to the elevator means at an elevated discharge portion thereof for directing the material to the load being sampled.

8. A structure as defined in claim 2, wherein the sample tube means further includes support means comprising a tower mounted on the framework, a linear fluid motor connected to the framework and disposed within the tower, and a sheave assembly connected to the motor and to the casing for moving the casing as a function of the movement of the motor.

9. A structure as defined in claim 8, wherein the processing means comprises, in combination:
   (7) crusher means for receiving a sample from the core removal means and crushing the sample;
   (8) secondary sample means connected to the crusher means for separating out a predetermined portion of the crushed sample; and
   (9) collector means for receiving the predetermined portion of the sample and retaining same for analysis.

10. A structure as defined in claim 5, wherein the collector means includes indexing means comprising a container connected to the secondary sampler means for receiving the predetermined portion of crushed sample, which container has an inlet and outlet; a plurality of receptacle disposed in circular arrangement beneath the container, the indexing means including a turntable on which the receptacles are disposed for being rotated in a substantially circular orbit; and conduit means including a plurality of chutes connected to the receptacles and extending toward the container for selectively registering with the outlet of the container.

11. A structure as defined in claim 10, wherein the processing means further comprises:
   (10) material and return means connected to the secondary sampler means for returning to the load from which the sample was taken the sample less the predetermined portion of the sample retained for analysis.

12. A sample tube for obtaining a substantially vertical core sample of a stationary load which may include large pieces of hard material, comprising, in combination:
   (a) a longitudinally extending casing open at a lower end thereof and mounted for reciprocal movement along a substantially vertical path;
   (b) an auger rotatably mounted within the casing and extending substantially entirely the extent of the casing; and
   (c) a cutting head connected to the auger and disposed in the open end of the casing for cutting through the hard material prior to carrying of the material into the casing by rotation of the auger to which the cutting head is affixed;
   wherein the sample tube means further includes support means comprising a tower mounted on the framework, a linear fluid motor connected to the framework and disposed within the tower, and a sheave assembly connected to the motor and to the casing for moving the casing as a function of the movement of the motor.

* * * * *